(12) United States Patent
Nelson et al.

(10) Patent No.: US 6,564,104 B2
(45) Date of Patent: May 13, 2003

(54) DYNAMIC BANDWIDTH MONITOR AND ADJUSTER FOR REMOTE COMMUNICATIONS WITH A MEDICAL DEVICE

(75) Inventors: Chester G. Nelson, Plymouth, MN (US); Ronald A. Stauffer, Princeton, MN (US); Charles R. Stomberg, Forest Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 241 days.

(21) Appl. No.: 09/745,143

(22) Filed: Dec. 20, 2000

(65) Prior Publication Data

US 2001/0023360 A1 Sep. 20, 2001

Related U.S. Application Data

(60) Provisional application No. 60/173,083, filed on Dec. 24, 1999.

(51) Int. Cl.[7] .................................................. A61N 1/08
(52) U.S. Cl. ........................ 607/60; 600/300; 128/920
(58) Field of Search ................ 607/27, 30, 31, 607/32, 60; 600/300, 301, 345, 315, 481, 483, 484, 485, 509, 529; 128/899, 902, 903, 904, 905, 920, 923, 924; 705/2, 3, 28; 707/6; 709/204, 205, 230, 238, 245, 246

(56) References Cited

U.S. PATENT DOCUMENTS

| | | | |
|---|---|---|---|
| 4,218,738 A | 8/1980 | Matyas et al. ............... 705/72 |
| 4,326,098 A | 4/1982 | Bouricius et al. ........... 713/155 |
| 4,993,068 A | 2/1991 | Piosenka et al. ............ 713/186 |
| 5,048,085 A | 9/1991 | Abraham et al. ............ 713/159 |
| 5,148,481 A | 9/1992 | Abraham et al. ............ 380/46 |
| 5,348,008 A | 9/1994 | Bornn et al. ................ 600/301 |
| 5,375,604 A | * 12/1994 | Kelly et al. ................ 600/484 |
| 5,508,912 A | 4/1996 | Schneiderman ............... 705/3 |
| 5,730,720 A | 3/1998 | Sites et al. .................. 604/27 |
| 5,752,976 A | 5/1998 | Duffin et al. ................ 607/32 |
| 5,926,501 A | 7/1999 | Souissi et al. .............. 375/131 |
| 6,221,012 B1 | * 4/2001 | Maschke et al. ............ 600/301 |
| 6,250,309 B1 | * 6/2001 | Krichen et al. ............. 600/300 |
| 6,336,900 B1 | * 1/2002 | Alleckson et al. ........... 600/300 |
| 6,363,282 B1 | * 3/2002 | Nichols et al. .............. 607/30 |
| 6,385,593 B2 | * 5/2002 | Linberg ....................... 705/28 |
| 6,386,882 B1 | * 5/2002 | Linberg ....................... 607/32 |
| 6,442,433 B1 | * 8/2002 | Linberg ....................... 607/60 |
| 6,471,645 B1 | * 10/2002 | Warkentin et al. .......... 600/300 |

FOREIGN PATENT DOCUMENTS

| | | | |
|---|---|---|---|
| WO | WO/97/18639 | 5/1997 | |
| WO | WO 98/42407 | 10/1998 | |
| WO | WO 99/60926 | 12/1999 | ............ A61B/5/08 |

\* cited by examiner

Primary Examiner—Willis R. Wolfe
(74) Attorney, Agent, or Firm—Girma Wolde-Michael

(57) ABSTRACT

A communication system is provided which allows real-time communication between a deployed implantable medical device (IMD) and a computing resource capable of storing and distributing patient and device data. A deployed IMD may be polled by a network interface external to the host patient, and data may be received by wireless real-time communication in a manner which ensures secure and reliable information exchange. A bandwidth or baud rate monitor is used to verify the viability of the network-IMD connection for the intended use and then monitors the connection to ensure that bandwidth remains reliable. An alert feature notifies the user of any threatening bandwidth onset. This feature allows vibrant exchange of real-time information from the patient-IMD to a medical provider or system expert.

32 Claims, 5 Drawing Sheets

DYNAMIC BANDWIDTH MONITOR AND ADJUSTER FOR REMOTE COMMUNICATIONS WITH A MEDICAL DEVICE

CROSS-REFERENCE TO RELATED APPLICATIONS

This application claims the benefit of U.S. Provisional Application No. 60/173,083, filed Dec. 24, 1999, "Dynamic Bandwidth Monitor and Adjuster for Remote Communications With a Medical Device." The disclosure and drawings of the provisional application are specifically incorporated herein by reference.

FIELD OF THE INVENTION

The present invention generally relates to implantable medical devices (IMDs). Specifically, the invention pertains to an information network for remotely directing and managing patient device data retrieval and device instruction updates. More specifically, the invention enables monitoring, alerting and self configuration of bandwidth or data transfer between an IMD and an external remote device. The collected data may be reviewed by a clinician for appropriate real time therapeutic action as required, or it may be archived to compare patient history and for other future use.

The present invention is compatible and complementary with the elements disclosed in the following pending applications: "Medical System Having Improved Telemetry," filed Jul. 19, 1999, Ser. No. 09/356,340 now U.S. Pat. No. 6,298,271; "System and Method for Transferring Information Relating to an Implantable Medical Device to a Remote Location," filed on Jul. 21, 1999, Ser. No. 09/358,081, now U.S. Pat. No. 6,250,309; "Apparatus and Method for Remote Troubleshooting, Maintenance and Upgrade of Implantable Device Systems," filed on Oct. 26, 1999 Ser. No. 09/426,741 now U.S. Pat. No. 6,442,433; "Tactile Feedback for Indicating Validity of Communication Link with an Implantable Medical Device," filed Oct. 29, 1999, Ser. No. 09/430,708 "Apparatus and Method for Automated Invoicing of Medical Device Systems," filed Oct. 29, 1999, Ser. No. 09/430,208, now U.S. Pat. No. 6,385,593; "Apparatus and Method for Remote Self-Identification of Components in Medical Device Systems," filed Oct. 29, 1999, Ser. No. 09/429,956, now abandoned; "Apparatus and Method to Automate Remote Software Updates of Medical Device Systems," filed Oct. 29, 1999, Ser. No. 09/429,960, now U.S. Pat. No. 6,363,282; "Method and Apparatus to Secure Data Transfer From Medical Device Systems," filed Nov. 2, 1999, Ser. No. 09/431,881 "Implantable Medical Device Programming Apparatus Having An Auxiliary Component Storage Compartment," filed Nov. 4, 1999, Ser. No. 09/433,477, now U.S. Pat. No. 6,411,851; "Remote Delivery Of Software-Based Training For Implantable Medical Device Systems," filed Nov. 10, 1999, Ser. No. 09/437,615, now U.S. Pat. No. 6,386,882; "Apparatus and Method for Remote Therapy and Diagnosis in Medical Devices Via Interface Systems," filed Dec. 14, 1999, Ser. No. 09/460,580; "Virtual Remote Monitor, Alert, Diagnostics and Programming For Implantable Medical Device Systems" filed Dec. 17, 1999, Ser. No. 09/466,284, now U.S. Pat. No. 6,497,655; "Instrumentation and Software for Remote Monitoring and Programming of Implantable Medical Devices (IMDs), filed Dec. 21, 1999, Ser. No. 60/172,937; "Application Proxy For Telecommunication-enabled Remote Medical Access Instruments," filed Dec. 23, 1999, Ser. No. 60/173,081; "Information Network Scheme For Interrogation Of Implantable Medical Devices (IMDs)," filed Dec. 24, 1999, Ser. No. 60/173,064; "Medical Device GUI For Cardiac Electrophysiology Display And Data Communications," filed Dec. 24, 1999, Ser. No. 60/173,065; "Integrated Software System For Implantable Medical Device Installation And Management," filed Dec. 24, 1999, Ser. No. 60/173,082; "Dynamic Bandwidth Monitor And Adjuster For Remote Communications With A Medical Device," filed Dec. 24, 1999, Ser. No. 60/173,083 "Large-Scale Processing Loop For Implantable Medical Devices (IMDs)," filed Dec. 24, 1999, Ser. No. 60/173,079; "Chronic Real-Time Information Management Systems For Implantable Medical Devices (IMDs)," filed Dec. 24, 1999, Ser. No. 60/173,062; "Automatic Voice and Data Recognition For Medical Device Instrument Systems," filed Dec. 24, 1999, Ser. No. 60/173,071 "Central Switchboard to Facilitate Remote Collaboration With Medical Instruments," filed Dec. 24, 1999, Ser. No. 60/173,080; which are all incorporated by reference herein in their entireties.

BACKGROUND OF THE INVENTION

In the traditional provision of any medical services, including routine checkups and monitoring, a patient is required to physically present themselves at a provider's office or other clinical setting. In emergency situations, health care providers may travel to a patient's location, typically to provide stabilization during transport to a clinical setting, e.g., an emergency room. In some medical treatment applications, accepted medical practice for many procedures will naturally dictate physical proximity of medical providers and patients. However, the physical transport of patients to clinical settings requires logistical planning such as transportation, appointments, and dealing with cancellations and other scheduling complications. As a result of such logistical complications, patient compliance and clinician efficiency may suffer. In certain situations, delays caused by patient transport or scheduling may result in attendant delays in detection of medical conditions including life-threatening situations. It is desirable, therefore, to minimize situations in which the physical transport of a patient to a clinical setting is required. It may also be desirable to minimize the extent to which a patient or patient information must be considered by a clinician at a particular time, i.e. during an appointment.

After the implantation of an IMD, for example, a cardiac pacemaker, clinician involvement with respect to the IMD has typically only begun. The IMD usually cannot be merely implanted and forgotten, but must be monitored for optimal results, and may require adjustment of certain parameters or settings, or even replacement, in response to or in anticipation of changes in patient condition or other environmental factors, or based on factors internal to the device. IMDs may also contain logic devices such as digital controllers, which may need to undergo firmware or software upgrades or modifications. In addition, information about the IMD may be gathered for treatment or research purposes. For example, many IMDs are capable of storing certain status information or other data regarding their operation internally.

Because IMD operation and patient physiology is preferably monitored to help effect the desired patient outcome, it would be desirable if data collected by an IMD could be viewed remotely and securely. Similarly, it would also be desirable that the instructions installed in an IMD may be modified in response to patient physiologic information, or perhaps be upgraded remotely as well.

In the event a change, modification or reprogramming of the IMDs is indicated, it would be desirable if the instruction could be implemented in the IMD as soon as possible, thus providing more continuous monitoring to proactively effect changes in the IMDs for efficient therapy and clinical care. This scenario may be contrasted with existing practice of responding to an adverse patient event or subjecting the patient to the inconvenience or expense of frequent in-person encounters with a clinician, for example after an unexpected therapy by the device, or to effect other monitoring of device functioning, e.g., spontaneous therapies by the device. For example, an implanted cardioverter defibrillator may administer to the host patient a cardioversion or defibrillation therapy. After such therapy, it is typically desirable to determine the parameters of, for example, an arrhythmia that a therapy was administered in response to, or of the therapy administered.

Despite the limitations of IMDs with regard to processing power, IMDs are in a unique position to monitor physiological systems continuously. High-resolution data can be collected, but implantable devices are ill suited to storage and processing of large amounts of complex physiological data. In contrast, computing power and data storage capacity (processor capability, memory, and adequate power supply) is abundantly available in the non-implantable ("external") world. The computing industry is still following Moore's Law (stating that transistor density will double every 18 months), delivering increasingly sophisticated computing devices yearly, and some of these gains accrue to the computer power of IMDs. However, frequent upgrading and replacement of IMDs based on more powerful models subjects a patient to additional stresses, and additional costs are imposed on the patient or health care system.

Prior art methods of clinical services, particularly IMD monitoring and adjustment, are generally limited to in-hospital procedures or other scenarios involving patient transportation to a clinical setting. For example, if a physician needs to review the performance parameters of an IMD in a patient, it is likely that the patient has to go to the clinic. Further, if the medical conditions of a patient with an IMD warrant a continuous monitoring or adjustment of the device, the patient would have to stay in a hospital indefinitely. Such a continued treatment plan poses both economic and social problems. Under the prior art, as the segment of the population with IMDs increases, many more hospitals and clinics, and attendant clinicians and service personnel will be needed to provide in-hospital service for the patients, thus escalating the cost of healthcare. Additionally, the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Such data is acquired by having the patient in a hospital/clinic to download the stored data from the IMD. Depending on the frequency of data collection, this procedure may pose serious difficulty and inconvenience for patients who live in rural areas or have limited mobility. Similarly, in the event a need arises to upgrade the software of an implantable medical device, the patient will be required to come into the clinic or hospital to have the upgrade installed.

Further, it is a typical medical practice to keep an accurate record of past and contemporaneous procedures relating to an IMD uplink with, for example, an IMD programmer, i.e. a computer capable of making changes to the firmware or software of an IMD. It is typically desired that the report contain the identification of all the medical devices involved in any interactive procedure. Specifically, all peripheral and major devices that are used in downlinking to the IMD may be reported. Currently, such procedures are manually reported, and require an operator or a medical person to manually enter data during each procedure. One of the limitations of such manual reporting procedures is the possibility for human error in data entry, or intentional tampering with data, thus motivating rechecking of the data to verify accuracy. Generally, the use of human clinicians and technicians to analyze data and implement changes in device therapy can result in inefficiencies and errors, absent intent to cause mischief or engage in untoward activities.

Yet a further condition of the prior art relates to the interface between a human operator and a programmer system. To aid a patient in the administration of a deployed medical device, clinicians such as pacing clinicians may be made available to implement desirable changes in the treatment regimen effected by an IMD. Generally, a medical device manager/technician should be trained on the clinical and operational aspects of the programmer. Under current practices, a technician may attend a class or training session sponsored by a clinic, a hospital, or the manufacturer to successfully manage a programmer-IMD procedure. Further, ideally the operator will keep abreast of new developments and new procedures in the management, maintenance and upgrade of the IMD. Accordingly, it is desirable that operators of programmers, IMDs, and related medical devices receive regular training or information about the IMDs they work with. This information will preferably be widely distributed, because IMDs, programmer devices, and related medical devices are distributed throughout the world. Further, the number of people having implanted medical devices has been increasing over the last few years, with an attendant increase in operator personnel. The total effect of these phenomenon is a widely dispersed and large body of operators. Thus, it is desirable to have a high efficiency communications system that would enhance data communications, both between the IMDs and medical instruments, such as programmers; and between operators and entities providing IMD updates and education such as manufacturers. However, despite any improvement in clinician communication and training that may be effected, it may be desirable to automate device administration, maintenance, and upgrading to the extent possible in order to ensure that device instructions and data are appropriate to the situation.

A further limitation of the prior art relates to the management of multiple medical devices in a single patient. Advances in modern patient therapy and treatment have made it possible to implant a number of devices in a patient. For example, IMDs such as a defibrillator or a pacer, a neural implant, a drug pump, a separate physiologic monitor and various other IMDs may be implanted in a single patient. To successfully manage the operations and assess the performance of each device in a patient with multi-implants may require frequent update and monitoring of the devices.

Confirmation and routine follow-up of basic device functioning following therapy events has been effected in the past using telephonic means. However, former methods of communication with medical devices did not provide for remote updating of software and firmware, or allow for operator training. In addition, former methods of communication with remote devices required the involvement of clinical personnel in the interpretation of data and prescription of treatment regimens or therapies. It would be desirable to remotely communicate information to and from implantable medical devices, and also provide for authentication of target device as well as confirmation of data integrity following the transmission of the patient data. Furthermore, it would be desirable to limit the degree to which human and particularly clinician involvement is required to effect the communication between an IMD and a remote resource.

Further, it may be preferred to have an operable communication between the various implants to provide a coordinated clinical therapy to the patient. Thus, there is a need to monitor the IMDs and the programmer on a regular, if not a continuous, basis to ensure optimal patient care. In the absence of other alternatives, this imposes a great burden on the patient if a hospital or clinic is the only center where the necessary upgrade, follow up, evaluation and adjustment of the IMDs could be made. Further, even if feasible, the situation would require the establishment of multiple service areas or clinic centers to support the burgeoning number of multi-implant patients worldwide.

SUMMARY OF THE INVENTION

The present invention provides a system for a clinician or other person or device to verify communication link bandwidth prior to and during real time data communications, greatly increasing the information security and reliability of the comprehensive system for managing the IMDs. For example, a referring physician could use this system feature to examine the patient remotely as a consultation system or for therapeutic intervention.

The invention also provides a computerized information network system linking one or more IMDs deployed in one or more patients to a computer via a data communication network. The network comprises: a first computer accessible by the network, and the first computer is capable of storing patient data recorded by an IMD; at least one network interface capable of wireless communication with at least one IMD deployed in a patient, with the network interface being capable of real-time communication with the network; and a bandwidth monitor for real-time monitoring of the available bandwidth during a real-time communication session between the IMD and the network interface.

The invention also comprises a computerized method of communicating real-time data from one or more IMDs deployed in one or more patients. The IMDs may have firmware or software. The invention comprises the steps of: communicating real-time bandwidth validation data signals between a user interface and an IMD and other network linked components; and upon verification of adequate bandwidth for an intended communication session, then transmitting via a network communication link real-time IMD-accessible data gathered from at least one of the IMDs to an external device capable of communicating real-time with a computing resource external to any patient. The method may further comprise the step of conducting real-time signal monitoring of the baud rate or bandwidth during the communication session and adjusting either the data being transferred or the available bandwidth to prevent loss of data during the communications session.

A technology-based health care system that fully integrates the technical and social aspects of patient care and therapy will preferably flawlessly connect the client with care providers irrespective of separation distance or location of the participants. Accordingly it is desirable to have a programmer unit that would connect to a centralized data source and repository. This may be termed, for example, a remote interrogator, or a remote data center. This remote data center will preferably provide access to an expert system allowing for downloading of upgrade data or other information to a local, i.e., IMD environment. Further, in one embodiment of the present invention, it is possible to enable the gathering of high resolution diagnostic/physiologic data, and to transfer information between the IMDs and a remote data center to dispense therapy and clinical care on real-time basis. Further, the data system contemplated by the present invention enables an efficient system for data storage, collection and processing to effect changes in control algorithms of the IMDs and associated medical units to promote real-time therapy and clinical care.

The proliferation of patients with multi-implant medical devices worldwide has made it imperative to provide remote services to the IMDs and timely clinical care to the patient. The use of programmers and related devices to communicate with the IMDs and provide various remote services has become an important aspect of patient care. In addition to the instant invention, the use of programmers may be implemented in a manner consistent with the co-pending applications detailed in the foregoing Cross Reference to Related Applications, and assigned to the assignee of the instant invention. In light of the disclosures of these incorporated references, the present invention provides a vital system and method of delivering efficient therapy and clinical care to the patient.

In a representative embodiment of the instant invention, one or more IMDs, such as a pacemaker, defibrillator, drug pump, neurological stimulator, physiological signal recorder may be deployed in a patient. This IMD may be equipped with a radio frequency transmitter or receiver, or an alternate wireless communication telemetry technique or media which may travel through human tissue. For example, the IMD may contain a transmission device capable of transmitting through human tissue such as radio frequency telemetry, acoustic telemetry, or a transmission technique that uses patient tissue as a transmission medium. Alternately, an IMD may be deployed in a fashion by which a transmission or receiving device is visible externally to the patient but is connected directly or via wires to the IMD. An external device, which may generally be termed an IMD Network Interface (IMDNI), may be positioned outside the patient, the IMDNI being equipped with a radio frequency or other communication means compatible with the communication media of the IMD or the IMD transmitter/receiver, which may be external to the IMD and may further be external to the patient. In an illustrative embodiment of the subject invention, IMDNI contains a radio frequency transmitter/receiver or similar radio frequency telemetry device. Communication may be effected between the IMD transmitter/receiver and the external IMDNI, e.g. via radio frequency. The IMDNI will be connected via a wireless or physical communication media, e.g. via modem and direct dial connection, with a data network, LAN, WAN, wireless, or infrared network. In an alternate embodiment of the subject invention, the IMDNI may have a direct connection or tunneled connection directly to the centralized computing resource. In yet another alternate embodiment of the subject invention, the system may be implemented as a data network that allows the IMDNI access to the computing center from many locations, for example providing for a IMDNI that is portable.

Using the computing power of external computing devices, the monitoring of long-term disease progression (e.g. heart failure, hypertension, diabetes) can be improved. Furthermore, therapies may be adjusted with finer granularity and improved results, with reduced need for human intervention and reduced opportunity for clinician error.

In addition to improved modeling of physiologic systems, the amount of historical data, particularly patient-specific historical data used as input to control systems can be virtually unlimited when it is stored externally to the patient. Furthermore, a more thorough comparison can be made between patients with similar diseases as data and therapy direction are centralized, which may be expected to result in gains to the body of medical knowledge and treatment efficacy. Data from other medical systems, either implanted or external, such as etiological databases, can be incorporated easily into the control system. Other anonymous patient experiences or treatment data may be more quickly incorporated into a subject patient's IMD regime than might be possible with existing systems of IMD programming or upgrading. In addition, a subject patient's own historical treatment parameters and corresponding outcomes may be used in making IMD programming and other treatment decisions.

The instant invention provides IMDs with access to virtually unlimited computing power as part of their data collection and therapy calculation processes. In an alternate embodiment of the present invention, the IMD may be used by an external computing device as a data collection agent, and as an agent to implement changes to a treatment regimen based on a complex dynamical or stochastic physiological model. Rather than continuously increasing the processing power of IMDs, the present invention provides a link with external computing power, which is more easily upgraded. In addition, control system algorithms based on current knowledge about physiologic systems could be more easily updated using a centralized powerful processor, rather than individually updating the firmware or software of thousands of deployed IMDs.

When multiple IMDs are deployed within a single patient, the data and therapy from these IMDs may be more easily and efficiently orchestrated, thus further improving treatment efficacy and convenience to the patient and clinician, and in some cases judiciously limiting clinician involvement. In addition, high resolution or finely grained data may be collected and stored from a vast number of subject IMDs. This finely grained patient data may be expected to prove valuable in defining and modifying an individual patient's treatment regimen as implemented by an IMD. In addition, this high-resolution data may be analyzed on a mass scale, providing opportunities for improvement of existing physiologic models. This data may serve, for example, to validate physiologic models being employed, or may suggest refinement of these models based on numerous patient outcomes.

This refinement of therapy and diagnostic algorithms or models may further be refined in conjunction with external medical devices as well. According to the present invention, IMD management and manipulation will be more efficient, secure and efficacious. For example, an embodiment of the present invention permits the use of complex control systems to manage therapy of implantable medical devices. In addition, the invention permits the orchestration of the data collection and therapy functions of IMDs, particularly the functions of multiple IMDs implanted in one patient. In addition, an embodiment of the present invention permits of centralized therapy prescription, and provides the ability to compare disease states, diagnostic data and therapy prescription across patients with fine granularity. The ability to update control system software and hardware at a central location is also provided, as well as the ability to upgrade the firmware or software in distributed deployed IMDs from one central location.

A communications system according to the present invention provides the ability to have high-power computing systems interact with implanted medical devices, thus providing the ability to use complex control algorithms and models in implanted medical devices. In addition, even with relatively simple modeling, or in stochastic models, relatively large amounts of historical data from a single or multiple medical devices may be brought to bear for predictive purposes in evaluating alternate therapy and IMD instruction prescriptions. The present invention provides a system that establishes an external communications device and data network as a 'data bus' for extending the processing power of deployed IMDs, while minimizing host patient and clinician inconvenience.

The present invention may be effected, in part, by the provision of an IMDNI device, which may be a stand-alone device or a computer peripheral device, that is capable of connecting an IMD, or simply data telemetrically received from an IMD, to a network or other data communication link. While the interface between a computer data link and an implanted medical device is referred to generally herein as a "Network Interface", or the like, it will be appreciated to those skilled in the art that the interface may serve as an interface to a variety of data communications systems, including not only networks, but also, without limitation, direct dial-up connections, dedicated lines, direct satellite links, and other non-network data communications connections.

In a preferred embodiment of the subject invention, a host patient, i.e., a patient having an IMD implanted within, presents themselves to a IMD network interface device, or IMDNI. This IMDNI will preferably have the capability of communicating with the IMD via wireless means, such as by radio transmissions. In one embodiment of the subject invention, the IMDNI may be placed, for example, in a patient's home, or may be available for use by several patients in a treatment facility such as a hospital, nursing home, or ambulatory care center.

In one embodiment of the invention, data can be interrogated, with the aid of a remote interrogator device, by an IMDNI in an emergency room and then uploaded to an information network to which a remote interrogator is connected. This information network may be according to any network protocol, for example, TCP/IP over the Internet. The uploading to a central interrogation computer may also be effected over a direct dial-up connection or a dedicated line. Upon uploading of the data, a medical professional or other clinician may be alerted to the fact the data has been uploaded. This clinician may then view the data. A patient could also interrogate his or her device at home and upload it for a medical professional or clinician to view later. Various scenarios according to the invention may provide convenient monitoring of IMD functioning to a host patient or clinician. For example, a patient may effect a test of their IMD with a device test such as an exercise or stress test in a more natural or real life scenario that may provide more reliable or accurate results than a clinical evaluation, in addition to providing increased convenience to the patient and reducing the need for clinician or other professional attention.

In this embodiment of the invention, for example, a host patient may effect a dial-up connection to a remote interrogator following an afternoon walk in their neighborhood or on a treadmill in their home. In addition to evaluation of device function during routine situations, according to this embodiment of the present invention, a home monitoring instrument may be provided to a host patient allowing the patient to send data, i.e., to effect remote interrogation, if, for example, they have a subjective belief that they are symptomatic. For example, a host patient of a cardioverter defibrillator IMD may effect remote interrogation if they believe they have suffered an arrhythmia event. The data resulting from the remote interrogation may then be made remotely accessible for evaluation by a pacing system expert. In a preferred embodiment of the subject invention, IMD function data and physiologic data of the host patient is made available nearly instantaneously to a clinician capable of evaluating the device function, physiologic event or data, or therapy administered by the target IMD.

In a preferred embodiment, the remote interrogator of the present invention is implemented as a software application which may be run on a server or central computer accessible via a network or direct connection by the IMDNI device. In an alternate embodiment, the IMDNI may be implemented as a software client which may run on a computer remotely from the interrogator server. Preferably, the remote interrogator program or device is capable of autonomously and dynamically determining the model of an IMD, for example, according to manufacturer, type, and model number, as well as the specific serial number of a particular device. When an IMD is within communication range of an IMDNI, the remote interrogator of the present invention is also preferably capable of configuring a deployed IMD, or commanding the IMDNI to retrieve data from the IMD.

In one embodiment, an interaction between a deployed IMD and the remote interrogator may take place within a discrete session. This session may encompass interrogation of one or more IMDs deployed in a single patient. In a representative embodiment, a session according to the present invention may proceed according to the following scenario. In order to begin an interrogation session, a host patient will typically present to an IMDNI. For example, the patient may place themselves in the vicinity of the IMDNI within range of the telemetry capacities of the IMDNI. This may take place at home in the case of an In Home Monitor (IHM) or at a medical facility such as an Emergency Room, Follow-up Clinic or Operating Room. At the initiation of a session, it will be preferable to configure the target IMD for optimal operation for remote interrogation. For example, the IMDNI may be programmed to issue a command to the target IMD to "Cancel Magnet", "Resume Therapy," or another command to enter a mode consistent with the interrogation process. Either prior to or after the establishment of a telemetry or other communication link with the target IMD, the IMDNI Operator will effect a communications link between the IMDNI and the remote interrogation computer. This IMDNI Operator may be a human attendant or technician, but preferably will be an automated module of the IMDNI firmware or software, or may be implemented as a software application on a general purpose computer connected to the IMDNI. Alternatively, the remote interrogator computer may lead a human or automated IMDNI through the steps of establishing a telemetry interface between the IMD and IMDNI; with the IMDNI in turn notifying the remote interrogator when a telemetry connection has been established. Communication with the remote interrogation server may be established via a network connection, such as a LAN or WAN. In this embodiment of the present invention in which the IMDNI is preferably attended by an operator, the operator may be the host patient of the target IMD, or it may be attendant personnel at a clinical setting. In either case, the operator may connect the IMDNI to a suitable network connection, if a network connection is not already in place. For example, a direct dial-up connection may be established in this manner by physically connecting the IMDNI into a telephone connection jack such as a RJ-11 analog jack. The operator at some point would turn the IMDNI on and cause the IMDNI system to dial a preconfigured telephone number. Alternately, other, more continuous types of network connections may also be established.

DETAILED DESCRIPTION OF THE DRAWINGS

Figure 1:
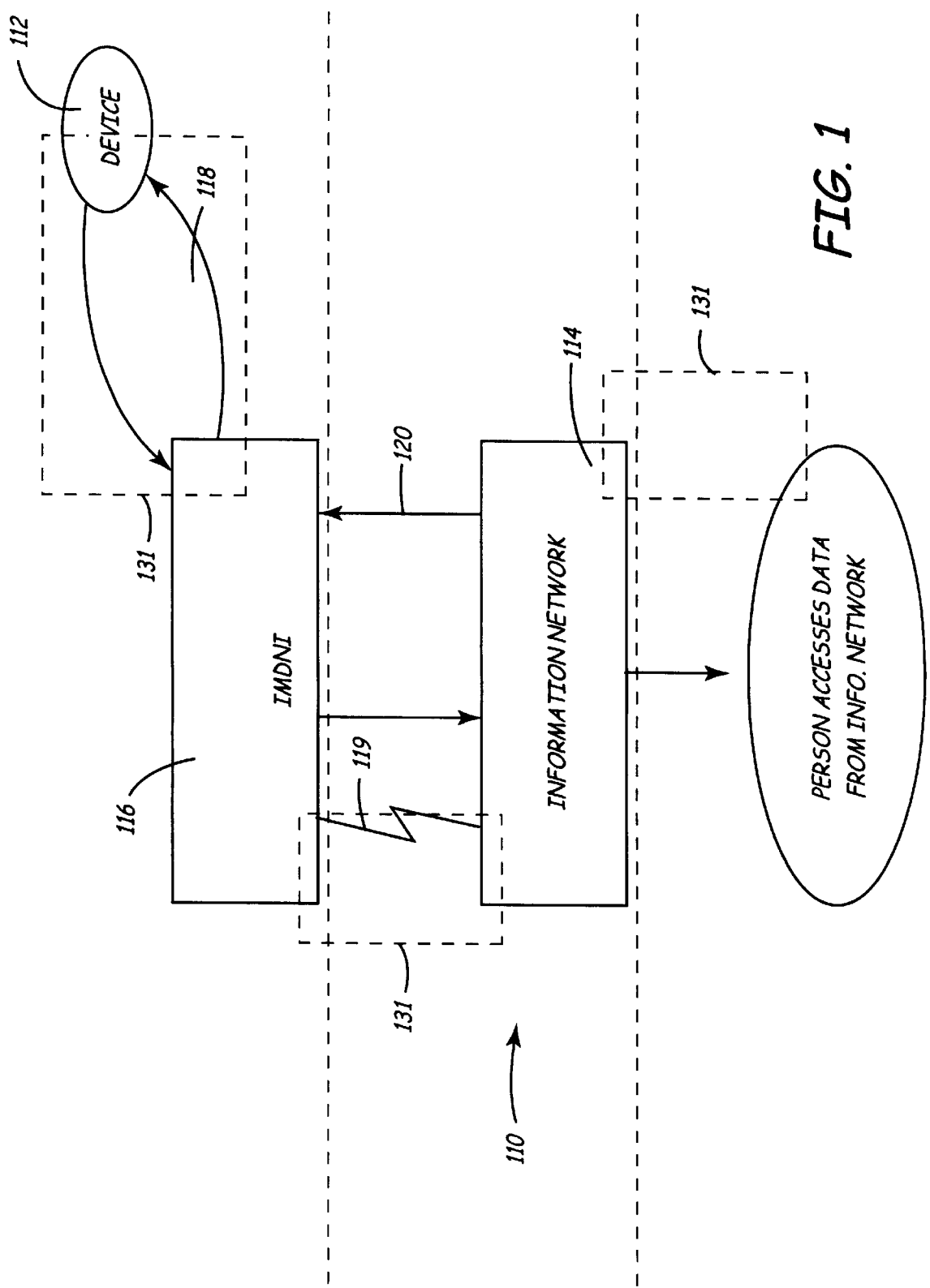
FIG. 1 depicts a general network architecture diagram of a system embodying the subject invention.

FIG. 1 depicts a general architectural view of a remote interrogation system according to an embodiment of the present invention. An IMD polling and interrogation system 110 is provided. IMD 112 has been deployed in a patient, for example, a patient at a location remote from remote interrogator connected to or within information network 114. The IMD 112 may be one of a number of existing or to be developed IMDs, for example, a pacemaker, defibrillator, drug pump, neurological stimulator, physiological signal recorder, oxygen sensor, or the like. A device external to the patient is provided which may be termed an IMD Network Interface, or IMDNI 116. This IMDNI 116 may communicate with the IMD 112 via, e.g., radio frequency, as discussed above. The IMDNI 116 may also communicate with a data network 114 via modem, LAN, WAN, wireless or infrared means according to network connections 119 and 120. This data network 114 is preferably able to communicate via a computer network or other suitable data communications connection with a central computer within information network 114. While in FIG. 1 a single IMD 112 is depicted, the subject invention permits of use with multiple IMDs deployed in a single patient, each making separate transmissions and receiving separate instructions from IMDNI 116. In an alternate embodiment of the subject invention, multiple IMDs deployed in a single patient are all linked to a single telemetry device implanted in a patient. This telemetry device may be separate from or incorporated into one of the IMDs deployed in a patient.

Returning to the single IMD embodiment depicted in FIG. 1, IMD 112 is equipped with or linked to a transmission and receiving device such as a radio frequency telemetry device, also preferably implanted in a patient. The information network 114 computing center or central computer preferably has sufficient computing power and storage capability to collect and process large amounts of physiological data using complex control systems. The patient is placed or places himself or herself in proximity to IMDNI 116. For example, IMDNI 116 may be placed in a patient's home, at their bedside perhaps, or may be placed in a community center, clinical office setting, nursing home, or other care facility. IMDNI 116 may also be embodied in a portable device that may be carried by the patient while outside the home or traveling. IMDNI 116, like IMD 112, contains or is linked to a communications media transmitter/receiver compatible with the type incorporated into or linked to IMD 112. In an illustrative embodiment of the subject invention, IMDNI 116 contains a radio frequency transmitter/receiver or similar radio frequency telemetry device establishing radio frequency link 118.

FIG. 1 also depicts user and instrument authentication/authorization means or sub-system 131, referred to generally as authentication system 131, implemented as an optional feature at one or more locations or times in the data transfer process. Authentication system 131 will be further discussed below.

Figure 2:
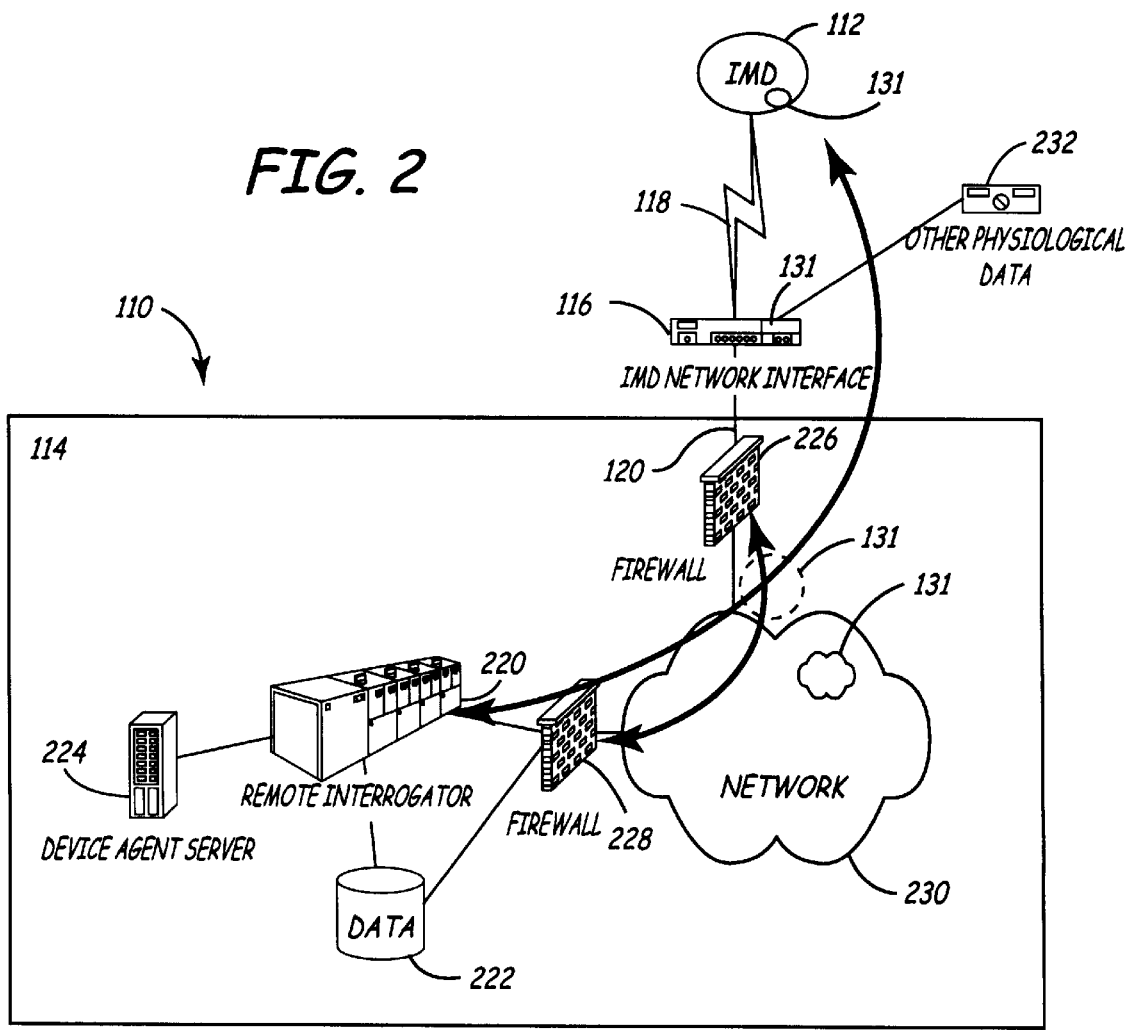
FIG. 2 depicts an implementation of the system of FIG. 1 using specific hardware components.

FIG. 2 depicts an implementation of the system of FIG. 1 using specific hardware components. As shown, information network 114 includes remote interrogator computer 220. Remote interrogator 220 will preferably be possessed of appreciably more computing power than possible with an IMD 112, in terms of processor speed, RAM available, and other data storage. Remote interrogator computer 220 is large scale in comparison to such processors that are available for incorporation into an IMD 112. For example, some commercially-available personal computers may contain sufficient computing power to operate as a server capable of carrying out many IMD 112 diagnostic, programming, and data storage tasks. In a preferred embodiment of the subject invention, however, remote interrogator 220 will be a mainframe, multi-processor supercomputer, or a multi-processor workstation, such as a type available from Silicon Graphics, Inc./SGI of Mountain View, Calif. Such relatively high-powered computing devices are better suited to calculations involving nonlinear systems and models such as those being developed to model physiologic systems.

Regardless of which computing device is used, in accordance with the present invention, the computing device will be configured as a server capable of communicating directly or indirectly with IMDNI 116. The computer 220 will preferably have sufficient storage, either internal to the computer or linked to the computer, for the storage of massive amounts of historical patient data from, for example, a particular patient having an IMD 112 in communication with computer 220, and/or subject data from relevant physiologic studies or from cohort groups having similar medical conditions and/or deployed IMDs. For example, as depicted in FIG. 2, remote interrogation computer 220 is linked to or contains data storage element 222. Data storage element 222 may contain any suitable means of data storage, including but not limited to hard drive, or another readable/writable magnetic or optical storage. In a preferred embodiment of the subject invention, data storage element 222 has a redundant array of disks such as a redundant array of inexpensive disks (RAID) system.

Security and integrity of the patient information and IMD interface operation will preferably be closely guarded and controlled for at least the following reasons: First, patient physiologic data detected by a deployed IMD 112 will be transmitted via IMDNI 116 to computer 116 for purposes of analysis of this data, and treatment regimens and/or IMD 112 instructions, firmware, or software may be changed on the basis of this information. Accordingly, integrity of transmitted data and instructions will preferably be maintained so as to avoid adverse patient outcomes or patient outcomes that do not take full advantage of the subject invention. In addition, patient information that may be linked to an identifiable individual is typically regarded as confidential. Accordingly, encryption or tunneling will preferably be provided to ensure patient confidentiality, particularly when transmissions between IMDNI 116 and computer 116 takes place though media other than a dedicated line/direct dial-up connection, such as a packet-based network technology over a public network or internetwork. For example, if the transmissions are routed over the Internet using TCP/IP, encryption will preferably be used. Examples of encryption, password and authentication schemes, generally, may include those contained in U.S. Pat. Nos. 4,218,738, 4,326,098, 4,993,068, 5,048,085, 5,148,481, 5,348,008, 5,508,912, and 5,730,720. Although known systems for encryption, password and authentication may be useful, they are not uniquely adapted to the requirements of the IMD interface system disclosed in this and related applications. Reliability of real-time communications flow may also be required in certain communication sessions where a programmer or a medical provider is using the IMD-patient feedback to effect change in the IMD or to conduct a diagnostic evaluation while monitoring both the IMD and the patient.

As an addition and alternative to the security systems noted above, a proprietary data exchange format/interface that is kept secret may be used in communications between IMD 112 and computer 116. However, even with secure dedicated lines or a secret data format, digital signatures will preferably be used to detect corruption of data. Additional implementations of security systems may also be utilized in accordance with the subject invention, including token-based and biometric security apparatus and methods to detect inalterable physical characteristics of persons attempting to access the patient data in order to authenticate the would-be user of the system and to ensure that the instrument being queried or otherwise used is proper. This is particularly important in distributed systems and systems permitting access to multiple IMDs, IMDNIs, or other components, or systems having multiple categories of users with different authorizations. Moreover, such systems as contemplated herein afford classification of users into categories where specialists would be allowed to use the validated instruments to interrogate and program IMDs, whereas non-specialists would only be able to interrogate such IMDs or related system components or data bases. This use of IMD and instrument-related authentication facilitates systemic efficiencies and patient compliance in manners not previously experienced or fully contemplated. Indeed, user interface is also enhanced by implementation of an option-rich authentication system 131. For example, one embodiment of the identification would be to automatically adjust system parameters to an authorized user's preference for screen displays, data emphasis, filtering, taskings, work flow schemes, feedback or reporting algorithms, and the like. Measures such as the foregoing may be used to authenticate the IMDNI 116 and IMD 112, as well as other system architecture or components, and for persons accessing patient data, including a host patient, field personnel, technical service representatives, data harvesters, data managers, medical providers, and other authorized users. Other examples of use include user authentication of a programmer, extender, or other sensitive or controlled aspects of a medical device data system, including reports and system configurations.

Security may also be effected as detailed in co-pending application entitled "Application Proxy for Telecommunications Enabled Remote Device Access Instruments", filed on date even herewith, Attorney Docket No. P8745, Ser. No. 09/731,222, which is hereby incorporated by reference in its entirety.

Accordingly, one embodiment of the subject invention utilizes digital signatures and encryption of the patient information and IMD 112 instructions being transmitted according to the present invention. Encryption of patient information will serve to protect patient confidentiality.

Each transmission of patient data will preferably have a digital signature that can be checked against the transmission payload to ensure that patient data and IMD 112 instructions were not corrupted during transmission. Examples of encryption/digital signature schemes that should prove sufficient for suitable encryption of patient information and digital signatures include PGP, the RSA public key infrastructure scheme, or other consumer-level or higher, prime number based encryption signature scheme. Biometric data used to authenticate and verify accessors of the data may include retina scans, iris scans, fingerprint scans, veinprint scans, voiceprints and other voice recognition techniques, characteristics, facial geometry/facial recognition according to facial nodal points, or hand geometry scans. These authentication techniques may be granted to primary users as well as to secondary users, such as for approved technical service personnel to effect override for instrument maintenance or emergency situations. In addition to various biometric and encryption techniques, instrument or IMD-related authentication mechanisms may include validation through use of: approved serial numbers, fixed or pre-loaded data signatures in the instrument or IMD memory, resistance or other electrical or digital characteristic matching, load recognition, or a data message generated by one or more pre-determined algorithms based on date, event, serial number, or other phenomenon. The use of one or more trusted systems within a medical device system, such as IMD polling and interrogation system 110, enables great advantages not previously achieved. For example, remotely located components may optimize use of wireless electronic transmissions of instrument serial numbers or like data which require validation of IMD data and unique patient biometric data, perhaps all within a certain timeframe, to permit certain types of update data transactions. Certain devices are much more conducive to visual scanning authentication means rather than data matching or key-based (encryption-based) systems, and these may thus be combined and optimized into redundant authentication system means for achieving the security, reliability and performance objectives of IMD-related systems. These authentication system 131 techniques may be used vertically i.e. IMD-IMDNI-NETWORK, as well as horizontally among IMDNIs, or other corresponding levels of device or system components. Indeed, this invention contemplates use of historical or contemporaneous patient biological data as another authentication tool for unique patient or IMD identification. Access to such unique data by patient, i.e., data not visually obtainable, is considered by the inventors to be a dramatic improvement over any known authentication system, and of particularly high importance in the IMD field. Of course, this in turn permits improved algorithms or templates, as appropriate, to combine known authentication techniques with those identified herein to create a new class of secure interface and network security systems, with attendant benefits.

In addition to the above security implementations, a preferred embodiment of the subject invention incorporates firewall and/or proxy server technology, as indicated in FIG. 2 at firewalls 226 and 228. Such security measures not only protect patient data stored in data storage element 222 from access by unauthorized persons, but also protect IMDNI 116 and IMD 112 from improper snooping and/or improper instruction from negligent or unscrupulous persons that may have access to data network 230.

In addition to communicating with IMD 112 as discussed above, IMDNI 116 may communicate with a peripheral physiological data gathering device 232, which may for example be external to the host patient having implanted IMD 112. IMDNI 116 may also communicate with additional devices as detailed in FIG. 3, central information network 114 via a number of network schemes or connections, with regard to any of the OSI layers. The network is depicted generally at network cloud 230. For example, communication may be effected by way of a TCP/IP connection, particularly one using the Internet, as well as a PSTN, DSL, ISON, Cable Modem, LAN, WAN, MAN, direct dial-up connection, a dedicated line, or a dedicated terminal connection to a mainframe. Various persons 118 including clinicians or the patient having IMD 112 installed may access the patient's data from information network 114, as described herein. This reduces the need for onsite clinical visits by the patient.

Transmissions between an IMD 112 and IMDNI 116 or between peripheral physiological data gatherer 232, or other peripheral devices will also preferably be protected from transmission errors using similar encryption, authentication, and verification techniques to those discussed above, and/or wireless communication enhancement techniques such as wireless modulation or another suitable wide-frequency spectra technique. Optionally, encryption and/or authentication will be effected end-to-end, i.e., covering the entire transmission from IMD 112 to computer 220 or from computer 220 to IMD 112, rather than effecting one encryption/verification scheme between IMD 112 and IMDNI 116, and a different scheme between IMDNI 116 and computer 220. As an alternative to, or in addition to the above authentication scheme, radio frequency pulse coding, spread spectrum, direct sequence, time-hopping, frequency hopping, a hybrid spread spectrum technique, or other wireless modulation techniques may be employed in order to reduce interference between IMD 112 and other IMD or other wireless devices, and to generally offer improved accuracy, reliability, and security to transmissions between IMD 112 and IMDNI 116, may be used to avoid cross-talk or confusion among IMDs and/or IMDNIs in proximity to each other. For example, radio coding may be implemented to avoid transmission errors or device confusion between neighboring IMD 112 patients utilizing a device implementing aspects of the present invention in a managed-care setting.

Preferably, a data network is provided that allows the external communications device, or IMDNI 116, access to the computing center 220 from one of many possible locations. This provides portability to the administration of the IMDNI 116 and enhancement of patient lifestyle options.

Upon establishment of a network connection, or direct dial-up connection, a communications link is established over which the IMDNI 116 may establish a connection with the remote interrogator computer 220. The initial communication may focus on authentication of the IMDNI 116. This will preferably include verification that the IMDNI 116 is certified for interrogating IMDs, i.e., a verification process has established that the software and hardware revisions are current, and that the authentication information uniquely identifies a specific known IMDNI 116.

Further considering the steps in a representative embodiment of the invention in which the IMDNI is attended by an operator, the remote interrogator 220 may next instruct the IMDNI Operator such as a human user how to configure the telemetry interface 118 between IMDNI 116 and IMD 112. This would typically be specific for the type of IMD 112 being interrogated and might involve, for example, placing a programming head or wand near the IMD 112, or just positioning the patient and IMDNI 116 in proximity. The IMDNI 116 may then notify the remote interrogator computer 220 that a telemetry connection has been established.

Upon establishment of a telemetry interface, preferably remote interrogator 220 selects a proper device agent software application or module to interrogate the specific device 112. This software application may be accessed from, for example, a separate device agent software server 224, or may be accessed directly by remote interrogator computer 220 from data store 222.

In a representative embodiment of the invention, a device agent software module is selected to interface with a particular type or model of IMD 112. In an embodiment of the subject invention in which the IMDNI 116 is configured to dynamically identify an IMD 112 presented to it for remote interrogation, preferably an initial IMD 112 identification stage precedes the selection of device agent module. In an embodiment of the present invention configured or adapted for use with an in-home monitor device, preferably the IMDNI is pre-configured to work only with the specific device(s) implanted in an individual host patient of the residence.

Upon execution of the applicable software module, for example the device agent corresponding to the IMD 112 presented to the IMDNI 116, the remote interrogator computer 220 may retrieve certain pertinent data from the IMD 112, including physiologic data regarding the host patient stored in IMD 112 memory, stored power remaining, amount of drug remaining within the device, or hardware, software, or firmware version information, or other device status information.

Upon completion of the data retrieval operation, the remote interrogator 220 may signal the completion of the operation to IMDNI 116. Preferably, the remote interrogator 220 will then close the connection with IMDNI 116, for example after a disconnect request to the IMDNI 116, for example, as part of the implementation of a symmetric release to avoid possible loss of data. The IMDNI 116 may then terminate the telemetry or other wireless connection with the IMD 112. This may involve the issuance of instructions to a human IMDNI Operator, if applicable, to effect the termination in a certain manner, for example, by removing the IMDNI 116 from proximity to the host patient. Preferably, the IMDNI 116 will not terminate communication with the IMD 112 until after the connection with the remote interrogator 220 is released.

Figure 3:
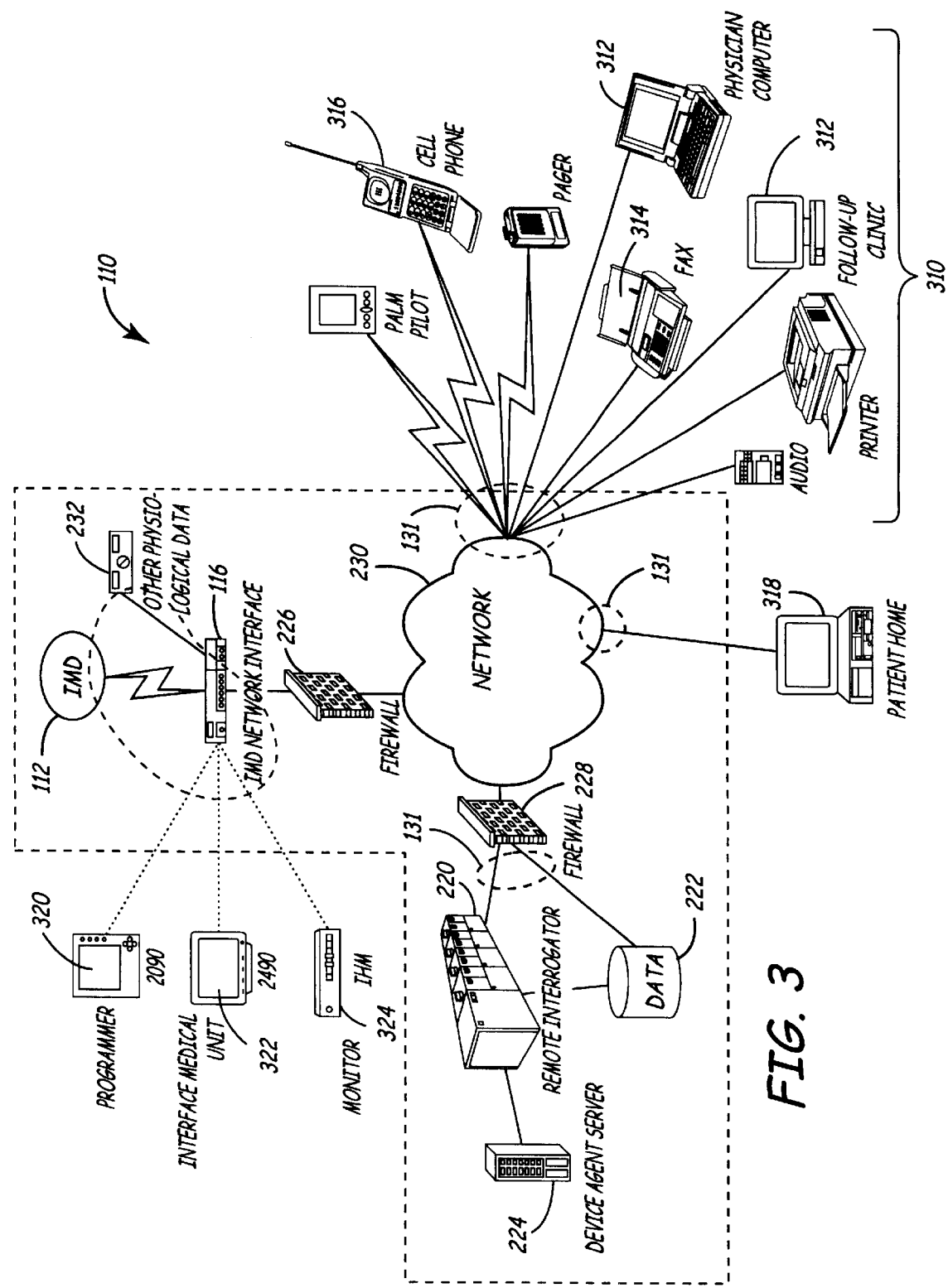
FIG. 3 depicts an alternate implementation of the system depicted in FIG. 1, including additional hardware devices.

FIG. 3 depicts an alternate implementation of the system depicted in FIG. 1, including additional hardware devices. As shown in greater detail in FIG. 3, once the data is collected from the IMDNI 116, notifications or confirmations may be generated by remote interrogator 220. These notifications may in desired cases be made available to remote data devices 310, such as a remote computer 312, fax machine 314, cellular telephone 316, or other data device which may be operated by or for individuals or entities interested in the target IMD 112 operation or host patient data. The data may also be provided to remote patient in-home personal computer 318. Preferably, these notifications may be accompanied by relevant data, and are made only to devices or individuals that have been properly authenticated as having permission to view the patient data. In addition, and particularly when provided to a remote computer 312 or 318, this data is preferably encrypted or digitally signed to preserve its confidentiality and for confirmation of data integrity. Various data communications methods may be suitable for transmission of the target device and host patient data to a remote computer, including an SMTP e-mail, UDP, FTP, or TCP/IP. In one embodiment of the present invention for example, properly authenticated interested parties may access the patient or device data, the data residing on a server such as the remote interrogator, via TCP/IP protocol using a web browser. It is also preferable that confirmation that the data has been retrieved successfully by the remote interrogator 220, or has been transmitted to a particular remote user such as a physician using remote computer 310, is transmitted to the site of collection and displayed on the IMDNI 116, or on a computer or other data device such as patient home computer 318. A confirmation that a remote clinician, for example, a clinician that is located somewhere other than the site of the IMDNI data collection point, or from the remote interrogator 220, has accessed the data via remote computer 310, may be transmitted to the site of collection 116 or to another location or device 310 or 318. This confirmation may be effected, for example, by a reply e-mail from a clinician that has received an SMTP message from remote interrogator 220, indicating that the data has been received or reviewed.

The present invention admits of various revenue-creating, or treatment administration or business applications. For example, prior to an appointment with a clinician, a pre-appointment interrogation may be effected using the system outlined above in order that the clinician may have reviewed or analyzed the relevant host patient or target device data prior to an in-person appointment by a host patient. In addition, a follow-up interrogation of a target device a certain prescribed time following an in-person appointment or other event may be provided for and automatically scheduled for execution by a IMDNI 116. For example, the IMDNI 116 may be programmed to poll for or otherwise attempt to establish telemetry or other data communication with a target device 112 at a certain time or interval; the success of the attempt possibly being contingent on the host patient being in proximity to the IMDNI 116 at the specified time, or on the connection of the IMDNI 116 being physically or otherwise connected to a data communications means such as a wireless connection or physical connection such as a RJ-11 phone jack. The present invention also admits of use during or following symptomatic events experienced by a host patient, providing for interrogation analysis and results. In any event, more convenient and/or more frequent patient monitoring and analysis is provided by the present invention, with a reduced reliance on in-person or on-site clinical visits by the host patient. In one embodiment of the present invention, the remote interrogation system described herein may be provided to a host patient or to a clinician or clinical entity on a subscription basis, or on a fee per use or per data access basis.

In operation, the deployed IMD 112 collects physiological data from the host patient via electrical, mechanical or chemical sensors, according to the type of IMD 112 deployed in the host patient. Some of this data may be used locally, i.e., processed and analyzed internally to the IMD 112 itself, to modify therapy or treatment on a 'real-time' basis. In addition, IMDNI 116 may access and store data from an IMD programmer 320, interface medical unit 322, or in-home monitor 324. Regardless of whether the physiological data from the host patient is used to modify therapy on this self-contained basis, the patient data will preferably be buffered, queued, or spooled in the IMD 112 until such time as the device is polled or "interrogated" by remote interrogator 220 IMDNI 116. During this transaction, the IMDNI 116 may also pass instructions received from the computing center 220 to the IMD 112.

IMDNI 116 may contact the computing center or central remote interrogator 116 and transmit the physiologic data uploaded from IMD 112 to IMDNI 116. The powerful computer(s) at the computing center 116 may store and/or process the data, perhaps combining it with historical data of the same type from the same device, or perhaps with data from other implanted and medical devices. For example, the physiologic data may be combined with anonymous data from other demographic or clinical groups consisting of subjects which may have data relevant or generalizable to host patient 114. For example, comparisons of the data collected may be made with data from other patients with similar disease states, and therapy solutions constructed and compared.

The computing center may then transfer instructions on modifications to therapy and data collection to the IMDNI 116. At the next opportunity for communications, the IMDNI 116 transfers the instructions to the IMD 112 and may also collect an additional batch of data buffered in the IMD 112. This opportunity for communication between IMDNI 116 and IMD 112 may not be immediately present. For example, IMD 112 within a host patient may be located away from IMDNI 116 temporarily, if the host patient has left their house or clinical setting where the IMDNI 116 is kept. An alternate barrier to IMDNI 116 to IMD 112 communication may be a poor environment for the communication media employed between the IMD 112 and the IMDNI 116.

Data may also be held at central computing center 220 or within IMDNI 116, for example, if the IMDNI 116 is carried by host patient 114 as a portable device, and an analog connection for a modem or suitable network connection may not be available.

In a preferred embodiment of the subject invention, communication system 110 will operate asynchronously, permitting for the possibility for breaks in the continuous and real-time communications and/or processing of the three subsystems (IMD 112, IMDNI 116, and remote interrogator 220). However, alternate embodiments of the invention are also possible, including synchronous, "real-time" control of the target IMD 112. This alternate "real-time" embodiment of the system 110 may be enhanced upon the establishment of more ubiquitous and robust communications systems or links.

However, as can be appreciated, during remote communications with an IMD the link may be interrupted or degraded due to various causes. This may be unacceptable or not a problem at all, depending on the loss tolerance of the data being transmitted. For example, some medical data being transmitted from the IMD may be of the type that a constant bit rate with few redundancies and a lower tolerance for data bit or packet loss is necessary. This type of data may require a different guarantee of service than other types of data, such as a lower level of guaranteed maximum delay or lower data loss.

Accordingly, when accessing an IMD as part of a remote real-time communication session (including, e.g., point-to-point and multi-access) it may be advisable to monitor the baud rate. This feature would then allow for a detection or early warning mechanism to be in place to alert the user of any difficulty with system capacity. Indeed, in at least one embodiment, it may be desirable to implement a feature which, at initial connection, will determine whether the baud rate or bandwidth of the communications link is at an acceptable level to conduct the data transfer anticipated. Various congestion management techniques may be employed using known scheduling theory and principles. Therefore, if a prescribed threshold, quality of service parameters/algorithms (e.g., peak cell rate, sustained cell rate, minimum cell rate, cell variation delay tolerance, cell loss ratio, cell delay variation, cell transfer delay, cell error ratio, severely-errored cell block ratio, cell misinsertion ratio, etc.) or margin of safety for baud rate is acceptable, then the communication session would be allowed to continue. If not, then termination may be suggested by any of various alert mechanisms, prompts, or automatic sequences. A new connection could be initiated, either automatically or by control of a user or a logic sequence. Although it is not normal for point-to-point communication links to deteriorate after connection is made, this feature would continue to monitor the baud rate and take appropriate action if a change is noted which is within or approaching a threshold. As appropriate, managers of a system may decide whether hard or soft real-time communications are needed in a dynamic manner or as a pre-set level with dynamic response capabilities during sessions. For example, although IMD-based real time data is quite important to preserve intact, it might be possible for the inventive feature to activate various traffic congestion control mechanisms which in turn could allow for network prioritization or allocation until the baud rate demand is lessened for the particular application in jeopardy. This may be particularly useful if the transaction involved real-time IMD (patient) feedback being analyzed to determine a therapeutic action or command which required communications integrity throughout the session.

As different data is transferred, different baud rates may be required. This feature of the invention also accommodates such changes in data load and monitors such changes, and in certain embodiments might be able to predict an imminent onset of such changes, in time to dynamically adapt the communications link to ensure safe and reliable data transmissions. For example, at certain times the user or programmer may wish to employ a voice over data feature to the patient having the IMD, to ensure simultaneous real time engagement with the patient during contact with, adjustment of, or information retrieval from an IMD. Alternatively, certain neural or cardiac waveforms, for example, may require a more robust baud rate capability than is possible. Depending on the circumstance, it may be very advisable not to initiate the data transfer if only an unstable communications link is available.

At other times the system might initially act in an asynchronous manner, where precise timing of data transfer and therapy changes is not as critical. As the device-instrument and network communications become more ubiquitous and less reliant on specific hardware (e.g. RF head, network cables), the control loop could become more time-dependent.

Figure 4:
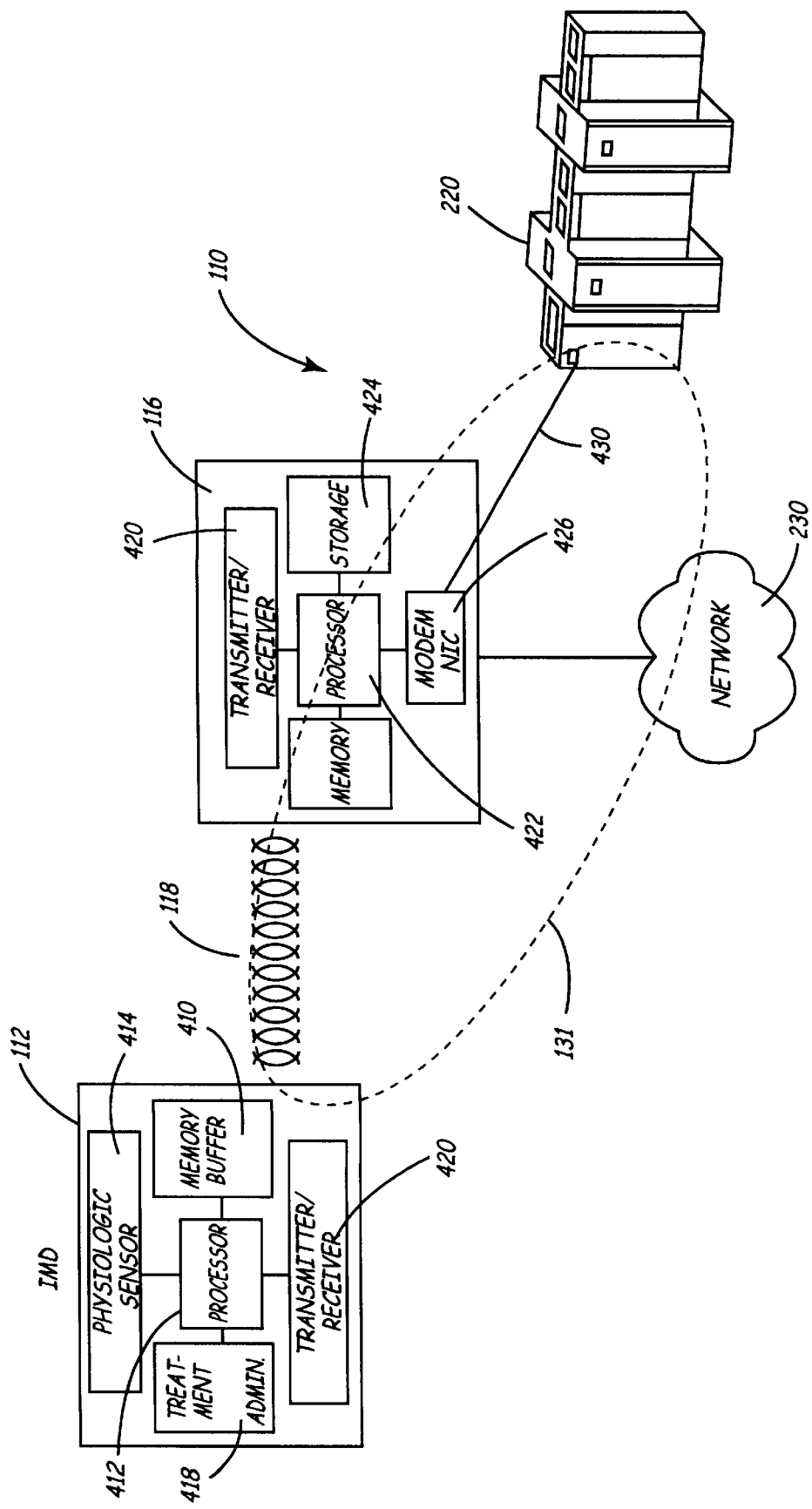
FIG. 4 is an architectural drawing of an embodiment of the subject invention showing internal device architecture.

FIG. 4 is an architectural drawing of an embodiment of the subject invention showing internal device architecture. As depicted in FIG. 4, IMD 112 effects the collection of high resolution physiological data; and provides for its temporary storage or buffering, for example in storage device 410. This storage device is preferably a RAM module of a type suitable for implantation in IMDs. Prior to storage in storage device 410, IMD processor 412 will preferably compress the physiologic data collected by physiologic sensor 414. IMD processor 412, in addition to processing the reception and storage of physiologic data, also preferably effects implementation of IMD 112 therapy, through treatment administration device 416. For example, and depending on the type of IMD 112 in which the subject invention is implemented, processor 412 may control the amount or frequency of electrical stimuli or drug delivered by treatment administration device 416. This control may be based on instructions originating from remote interrogator 220. FIG. 4 also depicts in greater detail the architecture of IMDNI 116 of FIG. 1. As shown in FIG. 4, IMDNI 116 contains a transmitter/receiver 420, a processor 422, storage device 424, and communication device 426. Communication device 426 may be, for example, a modem or network interface card. It may be seen in FIG. 4 that IMDNI 116 contains architecture components similar to those seen in a computer, and in an alternate embodiment of the subject invention, the communication system 110 of FIGS. 1–4 may be deployed with IMDNI 116 implemented as a computer with a peripheral device that may communicate with IMD 112. For example, IMDNI may be implemented together with a peripheral device to patient computer 318 of FIG. 3. As shown in FIG. 4, communications between IMDNI 116 and remote interrogator 220 may be effected either through a network 230, such as a LAN or the Internet, or communications may be effected through a direct dial-up or dedicated line, or through a terminal connection to a mainframe. These possible implementations are indicated generally by communications link 430. Typically, these connections may be considered alternatives, or both communications links, i.e., relatively direct link 430 and link through network 230 may be implemented in order to provide a backup communications system to the link used as the primary communication method.

In a preferred embodiment of the subject invention depicted in FIG. 4, remote interrogator 220 creates an instruction file for IMDNI 116 and/or for IMD 112. This file may consist largely of instructions for the IMD 112 affiliated with an IMDNI 116. Remote interrogator 220 may then contact IMDNI 116 to initiate transfer. Preferably, this method of contact will correspond to the method of communication from IMDNI 116 to central computer 220, although an alternate method may be used, particularly if a first preferred method proves unsuccessful. If communication with IMDNI 116 is possible, suitable instructions or information may be forwarded to IMDNI 116 for immediate or eventual communication to IMD 112.

While the instant invention has been described primarily with a single IMD 112 corresponding to a single IMDNI 116 and to a single central computer 220, alternative embodiments of the present invention are possible. For example, several IMDs 112, each with a separate identifying code or number, may utilize a single IMDNI 116. These several IMDs 112 sharing a IMDNI 116 may be deployed within a single patient, or the several IMDs 112 sharing a IMDNI 116 may be deployed in two or more separate patients, where each patient has reasonable access to the IMDNI 116 directly or to communications equipment which may send information to and receive information from IMDNI 116. While in an illustrative embodiment, several IMDNIs 116 share a single computer 220, alternative embodiments may have a single IMDNI 116 communicating with distributed or parallel computers 220, in addition to or in place of remote interrogator 220. In addition, an instruction regimen for a target IMD 112 may not be based solely on treatment considerations arising from patient data or from predictive modeling. In addition, an instruction regimen may contain firmware or software upgrades to target IMD 112 which are prescribed generally for all host patients of a particular IMD 112 model or type.

Upon establishment of contact between IMDNI 116 and IMD 112, an instruction regimen may be pushed or generally transmitted to IMDNI 116. IMDNI 116 or equivalent may then store the results of processing or instruction carried out by remote interrogator 220, for example, as dictated by device agent server 224. The IMD 112 instruction regimen prescribed by central computer 116 may be stored within IMDNI 116 indefinitely or for a fixed period of time prior to expiration. At the next opportunity for communication between IMDNI 116 and IMD 112, IMDNI 116 provides new therapy programming, as well as new instructions for data collection if necessary. In a preferred embodiment of the subject invention, if an instruction regimen has been received by IMDNI 116 for communication to target IMD 112, IMDNI 116 will periodically poll IMD 112 in attempts to establish a communication link, such as a wireless link. In an alternate embodiment of the subject invention, IMDNI 116 may have a display feature, which could be for example an LCD display or a simple indicator light indicating that an instruction regimen has been received for forwarding from central computer 220. A human user, for example, host patient of IMD 112 may press a button or otherwise initiate the process of communication between IMDNI 116 and target IMD 112. While IMDNI 116 is portrayed primarily as a self-contained or stand-alone unit, it will be appreciated that IMDNI 116 may also be implemented as a peripheral transmitter receiver capable of wireless communication with IMD 112, and also in communication with a computer such as patient home computer 318, such as a personal computer such as a laptop or portable computer. Computer 318 may also be a terminal of a remote computer 220. It will be appreciated that in the event that IMDNI 116 is implemented as a peripheral and terminal, some of the components of IMDNI 116, such as its storage component, may be implemented on a central computer 220 or storage device 222 rather than in the terminal implementing IMDNI 116. For example, the functions of IMDNI 116 of FIG. 2 may be implemented in software resident on routing computer 318. Communications interfaces of computer 318 when linked with IMDNI 116 may include a modem, network card, direct connection, or terminal connection. In this embodiment, preferably all data communication, security and message authentication and integrity confirmation as discussed above with regard to IMDNI 116 will be implemented on local computer 318. Communication between IMDNI 116, and central computer 220 may be implemented via network 230 or via direct connection. If IMDNI 116 is implemented on a computer such as a PC 318 of FIG. 3 with an IMDNI 116 transmitter/receiver peripheral device, a suitable pop-up message on the PC monitor may indicate a pending IMD 112 instruction or request, or an indicator on a display of the peripheral transmitter/receiver device 116 may indicate a pending instruction as above.

If an IMD 112 instruction regimen has expired prior to establishment of contact with the target IMD 112, IMDNI 116 may send an error message identifying the IMD 112 and/or instruction regimen by a suitable code. Upon reception of an error in instruction regimen transmission, central computer 220 may be programmed to carry out suitable updating of an instruction regimen, or an error message may be output to remote devices 310, a human operator or clinician for direct intervention by voice telephony or direct contact by mobile clinical personnel, for example.

Figure 5:
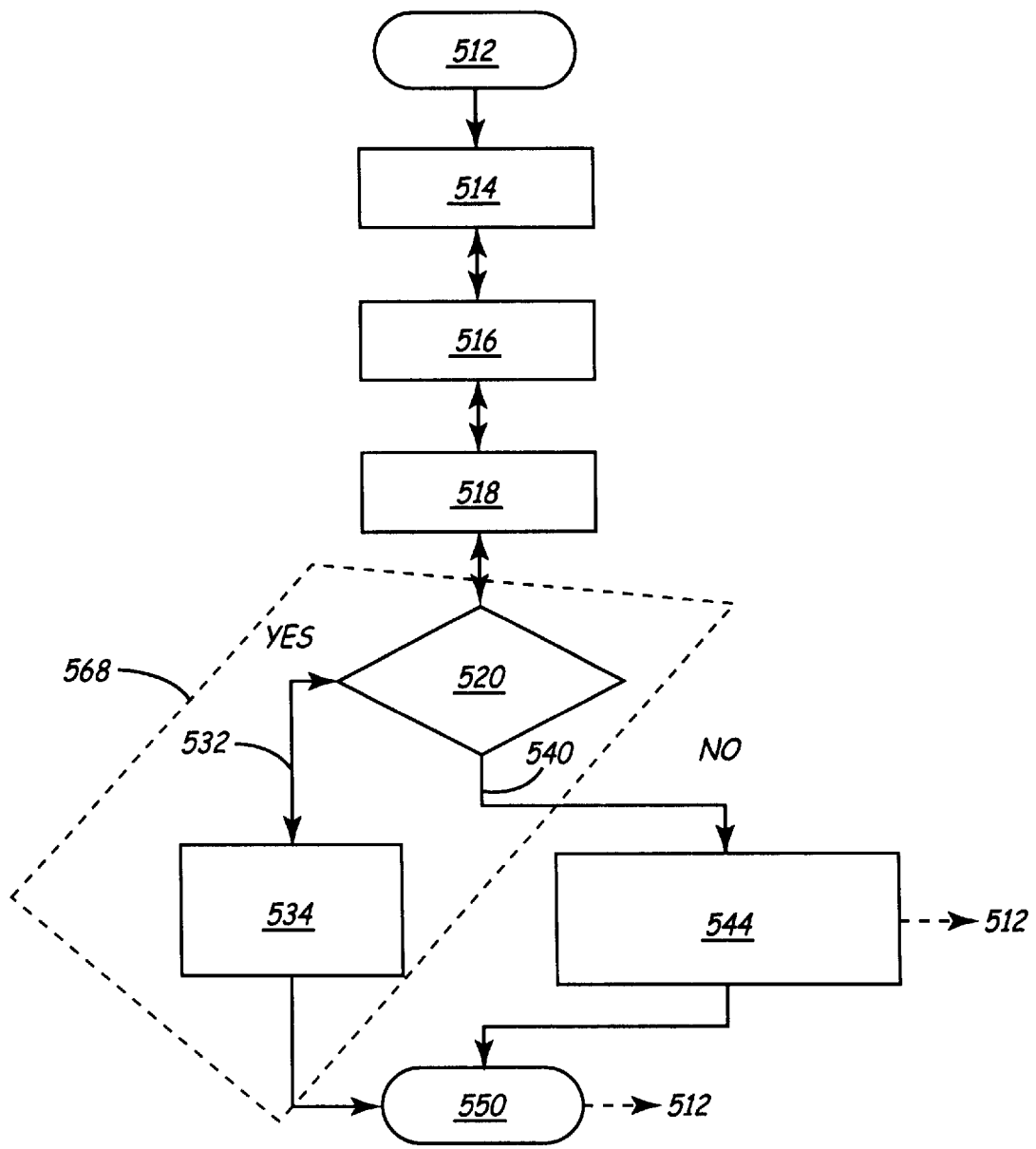
FIG. 5 is a flowchart of one embodiment of a bandwidth monitoring and alert process.

FIG. 5 is a flowchart of one embodiment of a real-time bandwidth monitoring and control feature or subsystem of the invention. Step 512 represents an initiation of a communications signal from a remote source to an IMD. Step 514 represents determination of the bandwidth or baud rate of the communications connection, and step 516 represents connection to and step 518 querying of the IMD. At step 520 a comparison is made to determine whether adequate bandwidth exists for the demand of the IMD data transfer and the capacity of the communications system or link. If the bandwidth is adequate, as described above by way of several different embodiments, then path 532 is granted, and data transfer may then commence at step 534. The bandwidth monitoring of real-time sessions is indicated by two way feedback data routing as shown between steps 514 and 534. At step 520, if the bandwidth is not sufficient, or is anticipated to be insufficient based on the anticipated data type or amount, then pathway 540 is granted, leading to no data transfer 544 and signal termination 550 or re-initiation at step 512. Optional traffic congestion control features to adjust network or other transmission capabilities are shown as adjustment template step 568, which may be activatable at various process points as shown by intersections in the flow lines with the template lines. Such optional traffic congestion control features are as described above and as are generally known in a network management context.

Although the invention is described with reference to particular embodiments, it will be understood to those skilled in the art that this embodiment is merely illustrative of the application of the principles of the invention. Numerous modifications may be made therein and other arrangements may be devised without departing from the spirit and scope of the invention.

What is claimed is:

1. A computerized method of communicating real-time data from one or more IMDs deployed in one or more patients, said IMDs having firmware or software, comprising the steps of:
   communicating real-time bandwidth validation data signals between a user interface and an IMD and another network linked component;
   verifying adequate bandwidth for an intended communication session;
   transmitting via a network communication link real-time IMD-accessible data gathered from an IMD to an external device capable of communicating real-time with a computing resource external to any patient; and
   conducting real-time signal monitoring of the baud rate or bandwidth during the communication session and adjusting either the data being transferred or the available bandwidth to prevent loss of data during the communications session.

2. A computerized information network system linking one or more IMDs deployed in one or more patients to a computer via a data communication network, said network comprising:
   a first computer accessible by the network, said first computer capable of storing patient data recorded by an IMD;
   at least one network interface capable of wireless communication with at least one IMD deployed in a patient, said network interface being capable of real-time communication with the network; and
   a bandwidth monitor for real-time monitoring of the available bandwidth during a real-time communication session between the IMD and the network interface.

3. The computerized network of claim 2, wherein the network comprises a direct link between the at least one network interface and the computer.

4. The computerized network of claim 3, wherein the first computer comprises a supercomputer.

5. The computerized network of claim 3, wherein the first computer comprises a multi-processor workstation.

6. The computerized network of claim 3, wherein the first computer comprises a networked or parallel cluster of computers.

7. The computerized network of claim 3, wherein the data communication is asynchronous.

8. The computerized network of claim 3, wherein the data communication is synchronous.

9. The computerized network of claim 3, further comprising a second computer on which device instructions or device operation and control software may be accessed by the first computer.

10. A computerized method of communicating real-time data from one or more IMDs deployed in one or more patients, said IMDs having firmware or software, comprising the steps of:
    communicating real-time bandwidth validation data signals between a user interface and an IMD and other network linked components; and
    upon verification of adequate bandwidth for an intended communication session, then transmitting via a network communication link real-time IMD-accessible data gathered from at least one of the IMDs to an external device capable of communicating real-time with a computing resource external to any patient.

11. The method of claim 10, wherein the network communication link comprises a radio frequency link.

12. The system of claim 10, wherein the one or more IMDs comprises one or more of a pacemaker, a PCD pacemaker/cardioverter/defibrillator, an oxygen sensing device, a nerve stimulator, a muscle stimulator, a drug pump, or an implantable monitoring device.

13. The computerized method of claim 10, comprising the further step of transmitting from the computing resource to one or more IMDs an upgrade to the IMD firmware or software.

14. The computerized method of claim 10 further comprising the steps of:
    determining instructions comprising an IMD treatment regimen based data gathered by or stored in the IMD; and
    transmitting via a network communication link the instructions to the appropriate IMD which may be executed by the IMD in accordance with its firmware or software.

15. The computerized method of claim 10, comprising the further step of transmitting from the computing resource to one or more IMDs a command to adjust a therapeutic or diagnostic feature of the IMD.

16. The computerized method of claim 10, further comprising the step of distributing the IMD data from the computing resource to one or more remote data interface devices.

17. The computerized method of claim 16 wherein the remote data interface device comprises one or more network computers, facsimile machine, telephone, voice mail systems, cellular devices, pagers, PDAs, printers, or broadcast reception devices.

18. The computerized method of claim 10, comprising the further step of conducting real-time signal monitoring of the baud rate or bandwidth during the communication session and adjusting either the data being transferred or the available bandwidth to prevent loss of data during the communications session.

19. The computerized method of claim 18, comprising the further step of alerting the user to the condition monitored.

20. The computerized method of claim 10 wherein the step of communicating real-time bandwidth validation data signals includes the step of detecting a communications link interruption.

21. The computerized method of claim 20, further comprising the step of re-initiating the step of communicating real-time bandwidth validation data signals if the bandwidth required for the communications session is restored.

22. The computerized method of claim 10, wherein the IMD-accessible data comprises physiologic data from the patient.

23. The method of claim 22, wherein the network communication link comprises a hybrid link.

24. The computerized method of claim 10, wherein the IMD-accessible data comprises device information.

25. The computerized method of claim 24, wherein the device information comprises hardware, firmware, or software identification information.

26. The method of claim 24, wherein the hybrid link comprises a radio frequency link from an IMD to a network interface, and a secondary network link from the network interface to the computer.

27. The method of claim 26, wherein the secondary network link is a direct dial up connection.

28. The method of claim 26, wherein the secondary network communication link comprises an asynchronous link.

29. The method of claim 26, wherein the secondary network communications link comprises a synchronous link.

30. The method of claim 26, wherein the secondary network link is an area network.

31. The method of claim 30 wherein the area network is a LAN.

32. The method of claim 30 wherein the area network is a WAN.

* * * * *